United States Patent

(12) United States Patent
Ishimaru et al.

(10) Patent No.: US 10,466,214 B2
(45) Date of Patent: Nov. 5, 2019

(54) IONIZATION DEVICE

(71) Applicant: HITACHI, LTD., Chiyoda-ku, Tokyo (JP)

(72) Inventors: Masako Ishimaru, Tokyo (JP); Masao Kamahori, Tokyo (JP); Masuyuki Sugiyama, Tokyo (JP); Kazushige Nishimura, Tokyo (JP); Hiroyuki Satake, Tokyo (JP); Hideki Hasegawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 15/764,249

(22) PCT Filed: Dec. 9, 2015

(86) PCT No.: PCT/JP2015/084505
§ 371 (c)(1),
(2) Date: Mar. 28, 2018

(87) PCT Pub. No.: WO2017/098600
PCT Pub. Date: Jun. 15, 2017

(65) Prior Publication Data
US 2018/0284083 A1 Oct. 4, 2018

(51) Int. Cl.
*H01J 49/16* (2006.01)
*G01N 30/72* (2006.01)
(Continued)

(52) U.S. Cl.
CPC ......... *G01N 30/7266* (2013.01); *G01N 30/02* (2013.01); *G01N 30/724* (2013.01);
(Continued)

(58) Field of Classification Search
CPC ...... H01J 49/165; H01J 49/161; H01J 49/162; H01J 49/164; G01N 30/02; G01N 30/7266; G01N 30/724
See application file for complete search history.

(56) References Cited

U.S. PATENT DOCUMENTS 4,531,056 A 7/1985 Labowsky et al.
6,777,672 B1 * 8/2004 Park .................... H01J 49/0404
250/281
(Continued)

FOREIGN PATENT DOCUMENTS

JP H9-304344 A 11/1997
JP 2000-106127 A 4/2000
(Continued)

OTHER PUBLICATIONS

International Search Report for related PCT application No. PCT/JP2015/084505, dated Mar. 15, 2016; English translation provided; 4 pages.

*Primary Examiner* — Wyatt A Stoffa
(74) *Attorney, Agent, or Firm* — Procopio, Cory, Hargreaves & Savitch LLP

(57) ABSTRACT

In order to implement a high-sensitivity mass spectrometry through an improvement in solvent removal efficiency during electrospray ionization and the like, an ionization device is provided with a light guide path 28 which guides light from a light source to sample microparticles generated by a micronization device to irradiate the microparticles. A closest distance d2 between a spatial area 34 in which the sample microparticles are present and a distal end 29 of the light guide path is greater than or equal to 0.1 mm and less than or equal to 20 mm. A closest distance d1 between an area of light irradiation 35 by the light guide path and any of a sample surface, a micronization device, and a sample holding unit that is the closest is greater than or equal to 0.01 mm and less than or equal to 10 mm.

21 Claims, 8 Drawing Sheets

(51) Int. Cl.
  *G01N 30/02* (2006.01)
  *F21V 8/00* (2006.01)
  *H01J 49/04* (2006.01)

(52) U.S. Cl.
  CPC .......... *G02B 6/0005* (2013.01); *H01J 49/044* (2013.01); *H01J 49/165* (2013.01); *G01N 2030/027* (2013.01)

(56) References Cited

U.S. PATENT DOCUMENTS

| | | | |
|---|---|---|---|
| 7,902,499 B2* | 3/2011 | Hiraoka | B82Y 35/00 |
| | | | 250/281 |
| 2004/0173743 A1* | 9/2004 | Valaskovic | H01J 49/165 |
| | | | 250/288 |
| 2008/0054176 A1 | 3/2008 | Hiraoka | |
| 2009/0071815 A1* | 3/2009 | Takamizawa | H01J 49/0059 |
| | | | 204/157.15 |
| 2011/0108726 A1* | 5/2011 | Hiraoka | H05H 1/2406 |
| | | | 250/282 |
| 2013/0015345 A1 | 1/2013 | Vertes et al. | |
| 2015/0053853 A1* | 2/2015 | Vertes | H01J 49/0404 |
| | | | 250/282 |
| 2016/0203966 A1* | 7/2016 | Vertes | H01J 9/0463 |
| | | | 250/288 |

FOREIGN PATENT DOCUMENTS

JP  2005-026159 A  1/2005
JP  4366508 B2  11/2009

\* cited by examiner

IONIZATION DEVICE

TECHNICAL FIELD

The present invention relates to an ionization device used for a liquid chromatography-mass spectrometry device and the like.

BACKGROUND ART

In order to perform mass spectrometry, it is necessary to extract from a sample a target substance in the form of a gas-phase ion, using an ionization device. Various ionization methods have been developed, such as electrospray ionization (ESI) capable of ionizing polar substances such as proteins; atmospheric pressure chemical ionization (APCI) capable of ionizing low-polarity substances; atmospheric pressure photoionization (APPI) whereby substance-selective ionization can be performed by irradiation of light absorbed by a specific substance; and matrix assisted laser desorption/ionization (MALDI) whereby a solid sample in which a matrix and a sample are mixed is dropped onto a plate and irradiated with laser for ionization.

Among others, ESI is being widely used in combination with a liquid chromatography-mass spectrometry (LC-MS) device to ionize a wide range of substances. In ESI, some of sample microparticles formed by a spray that failed to be completely desolvated may be discarded without being fed into the mass spectrometry unit, or may enter the mass spectrometry unit in the form of the original microparticles and detected as noise. In order to increase the sensitivity of mass spectrometry, it is necessary to increase the amount of ion that enters the mass spectrometry unit and to reduce noise by improving the efficiency of desolvation of the sample microparticles produced by spraying and increasing ionization efficiency.

In order to improve solvent removal efficiency, a method has been devised which promotes the vaporization of solvent from the sample microparticles using various heating means. For example, sample droplets sprayed by ESI are irradiated with light including infrared light to evaporate solvent from the droplets (Patent Literature 1). In another example, a spray tip distal end is irradiated with laser for heating (Patent Literature 2). In this example, a spray tip made from a material that does not absorb laser, such as diamond, is used. In another method, a sample solution attached to a needle or the needle itself is irradiated with laser light for ionization (Patent Literature 3). In yet another method, a heating gas is introduced into the spray area to heat the sample microparticles (Patent Literature 4). Another example uses an optical fiber to irradiate a sample on a sample holder with laser light to ionize a target substance in the sample (Patent Literature 5).

CITATION LIST

Patent Literature

Patent Literature 1: JP 2005-26159 A
Patent Literature 2: JP 4366508 B
Patent Literature 3: JP H9-304344 A
Patent Literature 4: U.S. Pat. No. 4,531,056
Patent Literature 5: U.S. Pat. No. 6,777,672 B1

SUMMARY OF INVENTION

Technical Problem

It has been discovered that in the configuration in which a spray liquid is irradiated with infrared laser across a large distance, the infrared laser is absorbed and attenuated by the solvent vapor filling the ionization chamber, and the efficiency of irradiation of the spray liquid decreases, resulting in a decrease in solvent removal efficiency.

In addition, when the spray tip or the sample itself is irradiated with infrared laser, the sample solution may bump and ionization may become unstable, resulting in a decrease in the quality of mass spectrometry data. In the method wherein the spray tip is made from a material that does not absorb light, such as diamond, a cost increase is incurred.

Solution to Problem

An optical fiber is installed in the vicinity of a spray, and sample microparticles are irradiated with infrared laser via an optical fiber. A spray tip and the optical fiber are arranged such that the sample microparticles immediately after the spray are irradiated but the spray tip is not irradiated with the laser.

The present invention provides an ionization device for ionization of a substance, the ionization device including a sample holding unit that holds a sample including a target substance; a micronization device that turns the sample being held by the sample holding unit into sample microparticles; a light source; and a light guide path that guides light from the light source to the sample microparticles generated by the micronization device to irradiate the sample microparticles. A closest distance between a spatial area in which the sample microparticles are present and a distal end of the light guide path is greater than or equal to 0.1 mm and less than or equal to 20 mm. A closest distance between an area of light irradiation by the light guide path and any of a surface of the sample, the micronization device, and the sample holding unit that is the closest is greater than or equal to 0.01 mm and less than or equal to 10 mm.

Advantageous Effects of Invention

According to the present invention, the irradiating light is guided via an optical fiber to the vicinity of the sample microparticles. Accordingly, attenuation of light due to absorption by vaporized solvent can be prevented, whereby solvent removal efficiency and mass spectrometry sensitivity are improved.

Other problems, configurations, and effects will become apparent from the following description of embodiments.

DESCRIPTION OF EMBODIMENTS

In the following, embodiments of the present invention will be described with reference to the drawings.

Figure 1:
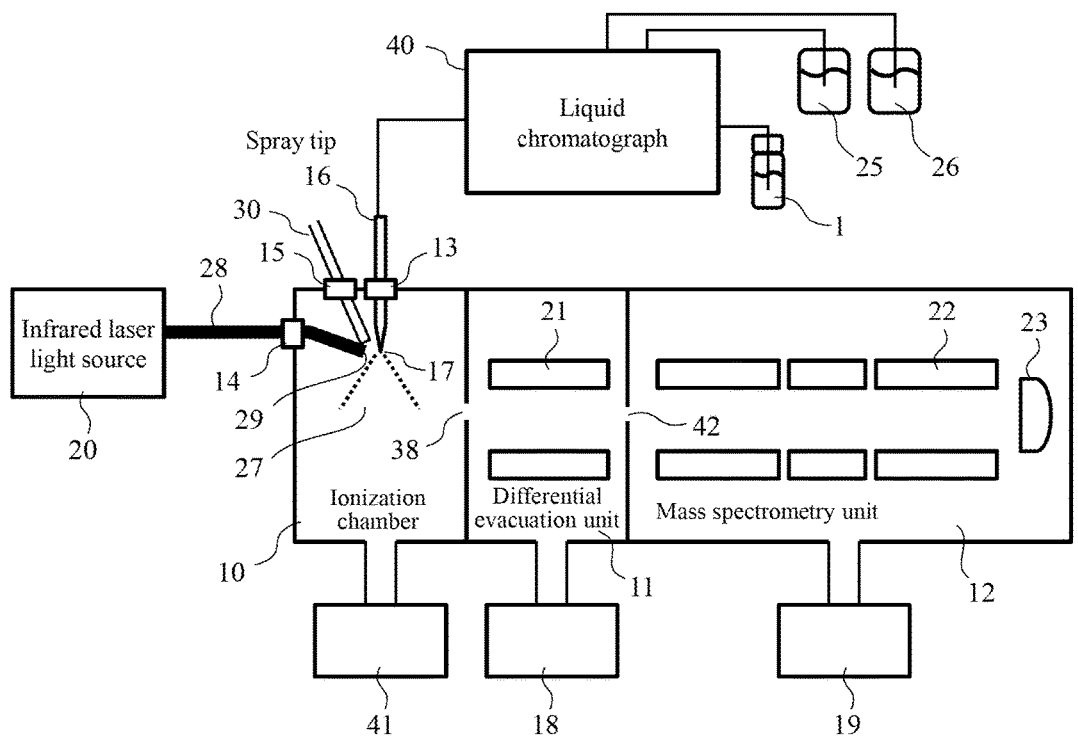
FIG. 1 is a schematic diagram illustrating a configuration example of a mass spectrometry device including an ESI ion source using the present invention.

FIG. 1 is a schematic diagram illustrating a configuration example of a mass spectrometry device including an ESI ion source in which the present invention is used. The mass spectrometry device is provided with an ionization chamber 10, a differential evacuation unit 11, and a mass spectrometry unit 12. The ionization chamber 10 is evacuated by a pump 41, and communicates with the differential evacuation unit 11 via a minute opening 38. The differential evacuation unit 11 is evacuated by the vacuum pump 18, and communicates with the mass spectrometry unit 12 via a minute opening 42. The mass spectrometry unit 12 is evacuated by a vacuum pump 19, and includes a mass separation device 22 and a detector 23. Into the ionization chamber 10, a spray tip 16 for ESI is introduced via a feedthrough 13 installed in a wall. An infrared laser light source 20 is provided externally to the ionization chamber 10. An optical fiber 28 is connected to the infrared laser light source 20. The optical fiber 28 is passed through a feedthrough 14 installed in a wall of the ionization chamber 10 and inserted into the ionization chamber 10, with an optical fiber distal end 29 positioned near a spray tip distal end 17. The ionization chamber 10 also has a gas introduction pipe 30 inserted therein via a feedthrough 15 to introduce a heated solvent removal gas.

Charged sample molecules produced in the ionization chamber 10 by a spray with the spray tip 16 are introduced via the minute opening 38 into the differential evacuation unit 11, and transported to the next minute opening 42 by an ion guide 21. The charged sample molecules that have passed through the minute opening 42 are subjected to an analysis by the mass separation device 22, such as a triple quadrupole mass separation device, in the mass spectrometry unit 12. The mass separation device may be of other types, such as a quadrupole type, a time-of-flight type, an ion trap type, or a magnetic field type. Instead of the differential evacuation unit 11 and the mass spectrometry unit 12, an ion mobility spectrometer or a high-field asymmetric ion mobility spectrometer may be used, whereby ions in a gas are moved in an electric field and separated depending on a difference in their mobility.

Figure 2:
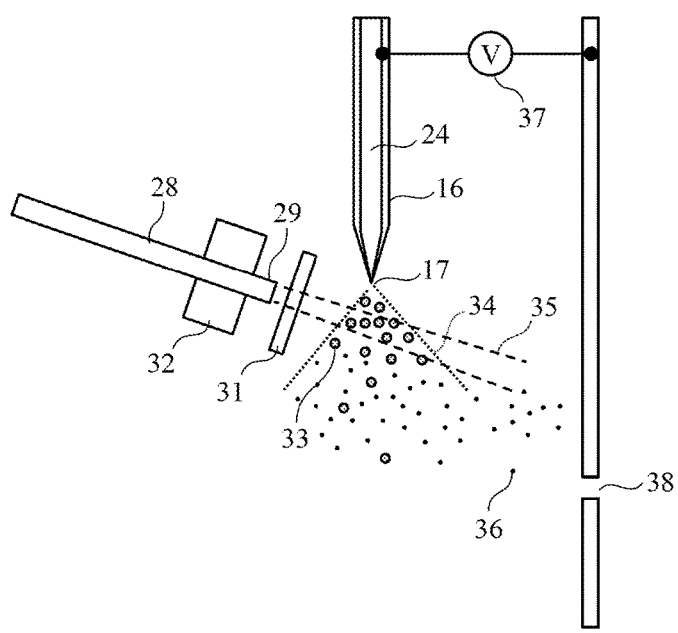
FIG. 2 is an enlarged schematic diagram illustrating an example of an ionization chamber.
Figure 3:
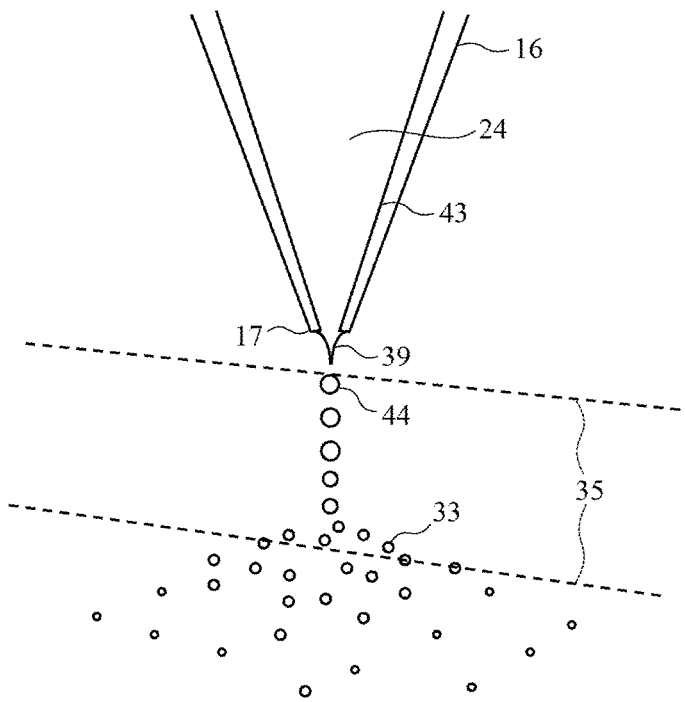
FIG. 3 is an enlarged schematic diagram of a spray tip distal end.

FIG. 2 is an enlarged schematic diagram illustrating an example of the ionization chamber 10. FIG. 3 is an enlarged schematic diagram of the spray tip distal end 17. To the spray tip 16, a high-voltage power supply 37 is connected. The spray tip 16 retains an eluate 24, which is a liquid including a sample molecule and solvent that has flowed from a liquid chromatograph (LC) 40, and sprays the eluate 24 from the spray tip distal end 17 into the ionization chamber 10, generating charged sample microparticles 33. Thus, the spray tip 16 in the example provides a sample holding unit, and at the same time functions as a micronization device.

The sample microparticles 40 immediately after the spray are charged microparticles of the eluate 24 with a diameter of not more than 10 μm. As the solvent vaporizes from the surface of the microparticles and the diameter of the microparticles decreases, gas-phase charged sample molecules 36 are eventually produced. In the case of positive ionization, the charged sample molecules 36 comprise neutral sample molecules to which one or a plurality of proton or metal ions, ammonium ions and the like are attached. If the efficiency of solvent vaporization (solvent removal) is high, the efficiency with which the charged sample molecules 36 are obtained also increases, and the analysis sensitivity increases.

In the present example, as a way to promote solvent removal, infrared laser generated by the infrared laser light source 20 is guided to the ionization chamber 10 via a light guide path, such as the optical fiber 28, and irradiated onto the sample microparticles so as to increase the temperature of the sample microparticles. Preferably, the wavelength of the infrared laser is selected such that the wavelength is absorbed by the solvent included in the sample microparticles 33. Under typical conditions for a liquid chromatograph, a C18 column is used, solvent 25 (A) is water, solvent 26 (B) is acetonitrile, and LC separation is performed in a gradient condition such that the mixture rate of solvent A to solvent B is linearly changed from 9:1 to 1:9. In this case, it is possible to use an infrared laser with a wavelength lying in the absorption band of water. Because water has a strong absorption band in the vicinity of a wavelength of 3 μm, an infrared laser with a wavelength of 3 μm enables efficient heating. Water generally has absorption from 1 μm to 100 μm, although with a smaller extinction coefficient than for the absorption peak of 3 μm. Accordingly, an infrared laser with an oscillation wavelength in a range of less than or equal to 1 μm and more than or equal to 100 μm may also be used, such as Er:YAG laser (2.9 μm), $CO_2$ laser (10.6 μm), other semiconductor lasers, and fiber lasers. On the other hand, acetonitrile has a relatively strong absorption peak around 7.0 μm, and also has absorption peaks at 3.2 μm, 4.3 μm, 9.5 μm, and 13.4 μm. Accordingly, a laser including such wavelengths as oscillation wavelengths may also be used.

In order to maintain a constant heating efficiency of laser absorption by solvent throughout the time periods of the solvent gradient condition, laser output is adjusted when a single laser is used. For example, when a laser with the absorption wavelength of 3 of water is used, a method may be contemplated that implements a program whereby laser output increases as the water content decreases. In the case of a pulse laser, laser output adjustment may be performed by varying the pulse period. By using a plurality of wavelengths of lasers and performing irradiation at both the water absorption wavelength of 3 μm and the acetonitrile absorption wavelength of 7 μm, a constant solvent removal efficiency can be maintained even if the solvent mixture rate is changed. As the light source, an infrared lamp may be used instead of infrared laser. The infrared lamp provides infrared light of continuous wavelengths. Accordingly, while the infrared lamp may be inferior to laser heating in terms of the amount of heat at specific wavelengths, it can accommodate the absorption wavelengths of various solvents. In any of the cases of light source, the light used for solvent removal is guided via the light guide path, such as an optical fiber, to the vicinity of the distal end of the spray tip 16 in the ionization chamber 10, and irradiates the sample microparticles.

As illustrated in FIG. 2, the distal end portion of the optical fiber 28 is fixed on a position adjustor 32 for position adjustment. The position adjustor 32 comprises, e.g., an xyz stage capable of position adjustment to the accuracy of 0.01 mm. The increase in the width of the laser light is adjusted with the lens 31. As illustrated in FIG. 3, the spray tip distal end 17 has an opening portion with a diameter on the order of 1 to 50 μm. A tip inner surface 43 is in contact with the sample solution. At the opening portion, a liquid level 39 of the sample solution is formed. From the liquid level 39 of the sample solution, the sample microparticles 33 with a diameter on the order of 0.1 μm to 10 μm are emitted into the space inside the ionization chamber 10. The position, direction, and expanse of the laser light are set such that the laser light does not irradiate the spray tip distal end 17 but irradiates the sample microparticles 33 or the sample microparticles 40. In this way, the solvent included in the sample microparticles absorbs the infrared light and generates heat, whereby vaporization of solvent (solvent removal) is promoted. Because the spray tip 16 and the sample solution therein are not directly hit with the laser light, the phenomenon can be prevented in which the eluate 24 in the spray tip distal end 17 or the spray tip 16 is hit with laser light and over-heated, causing the eluate 24 to bump at the spray tip distal end 17 and making ionization unstable. The material of the spray tip may be conventional SUS or silica, for example, and may be manufactured at low cost.

In addition, by installing a lens 31 and the optical fiber distal end 29 outside the sample microparticle spray area 34, it becomes possible to prevent a decrease in laser light transmission due to contamination of the optical fiber distal end 29 caused by the attachment of the sample microparticles 33 thereto.

If the laser light enters, via the minute opening 38, the differential evacuation unit 11 and further the mass spectrometry unit 12 and reaches the detector 23, the laser light may be detected as noise, resulting in a decrease in the quality of mass spectrum. By adjusting the position and direction of the optical fiber distal end 29 and the expanse of the laser light so that the laser light does not enter the detector 23, it becomes possible to prevent the laser light from being detected as noise.

The ionization chamber 10 is filled with the solvent vapor of the sprayed sample solution. The ionization chamber 10 may be evacuated with the pump 41 to a pressure on the order of 0.01 atm. By placing the ionization chamber 10 in a pressure range of greater than or equal to 0.01 atm and less than or equal to 1 atm, the partial pressure of the solvent vapor is decreased and solvent removal is promoted.

Meanwhile, laser light has the problem of being absorbed and attenuated by the solvent vapor filling the ionization chamber 10. Accordingly, solvent removal efficiency can be improved when the optical fiber distal end 29 is disposed as close to the sample as possible. Because LC often involves the use of water as solvent, laser light absorption by water vapor is estimated below. Transmission of light is given by the following expression using extinction coefficient k ($cm^{-1}$ $atm^{-1}$), incident light amount $I_0$, transmitted light amount I, water vapor partial pressure P (atm), and optical path length L (cm):

$$I/I_0=\exp(-kPL)$$

The extinction coefficient k of water vapor at a wavelength of 3 μm is approximately 1 $cm^{-1}$ $atm^{-1}$. From the foregoing, the transmission of light with a wavelength of 3 μm when P=1 atm with respect to various optical path lengths is computed as follows.

| Optical path length | Transmission |
|---|---|
| 100 mm | $5 \times 10^{-5}$ |
| 50 mm | $7 \times 10^{-3}$ |
| 20 mm | 0.1 |
| 10 mm | 0.4 |
| 2 mm | 0.8 |

That is, by making the distance between the optical fiber distal end 29 and the sample microparticles 33 less than or equal to 20 mm, it becomes possible to utilize 10% of the energy of incident laser light for solvent removal. Further, by making the distance less than or equal to 10 mm, it becomes possible to utilize 40% of the energy of incident laser light for solvent removal. More preferably, by making the distance less than or equal to 2 mm, it becomes possible to utilize 80% of the energy for solvent removal. Thus, by decreasing the distance between the optical fiber distal end 29 and the sample microparticle spray area 34, the energy of laser light can be efficiently utilized for solvent removal. Incidentally, in the case of a conventional example in which sample droplets sprayed by ESI are irradiated with light including infrared light without using an optical fiber, the distance from the light source to the sample droplets is on the order of 50 mm. In this case, the transmission is estimate to be $7\times10^{-3}$. As will be appreciated from the above, in the conventional light irradiation method, most of the optical energy that should be utilized for solvent removal is absorbed by the atmosphere of the ionization chamber 10, making the method less efficient.

As illustrated in FIG. 3, in ESI, under appropriate conditions of flow rate and voltage, a sample liquid surface 39 forms a cone referred to as a Taylor cone at the spray tip distal end. From the distal end of the Taylor cone toward the opposite end, a jet release of the sample microparticles 44 is generated (cone-jet mode). The droplets are further broken up into fine droplets 33, and the fine droplets form a spatially expanded plume due to Coulomb repulsion. Accordingly, in order to efficiently utilize optical energy for solvent removal, laser may irradiate a jet portion in which the sample microparticles are not spatially expanded, or a spatial area at the boundary between the jet where the droplets begin to be broken up and the plume. The jet portion has a length on the order of 0.01 mm to 2 mm from the Taylor cone distal end, depending on the spray distal end diameter or flow rate, and it is most efficient to irradiate the portion with a laser spot of the same order of diameter as the length of the jet. It should be noted, however, that the positional relationship between the spray tip distal end and the optical fiber distal end may vary by 0.1 mm or so during measurement, due to device vibrations and the like. Accordingly, in order to prevent a spray from becoming destabilized as the laser light hits the spray distal end due to displacement caused by vibrations, it is preferable that there is a distance of at least 0.1 mm between the spray distal end and a laser irradiation area 35. In addition, while depending on the spray tip distal end diameter or flow rate, the diameter of the spatial expanse of the plume takes a value on the order of 1 mm to 10 mm at a distance of 5 mm from the spray tip distal end. Accordingly, when the plume is irradiated with laser, the irradiation may be performed with laser light having an expanse comparable to the diameter of the microparticle expanse, whereby it becomes possible to perform solvent removal efficiently.

Further, by introducing heated dried inert gas (solvent removal gas) into the ionization chamber 10 via the gas introduction pipe 30 and contacting the gas with the sample microparticles, solvent removal efficiency can be improved, and discharge from the spray tip distal end 17 can be suppressed, whereby it becomes possible to stable ionization.

Example 1

Figure 4:
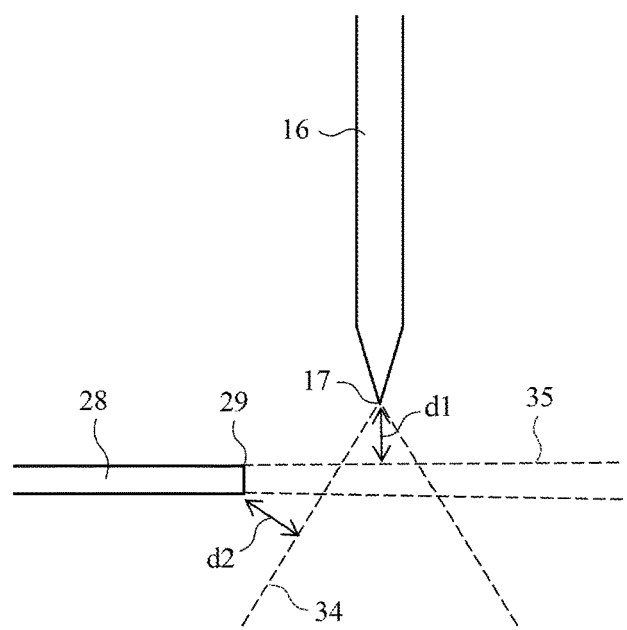
FIG. 4 is a schematic diagram illustrating an example in which the central axis of the spray tip and the central axis of the optical fiber are arranged in a perpendicular positional relationship.
Figure 5:
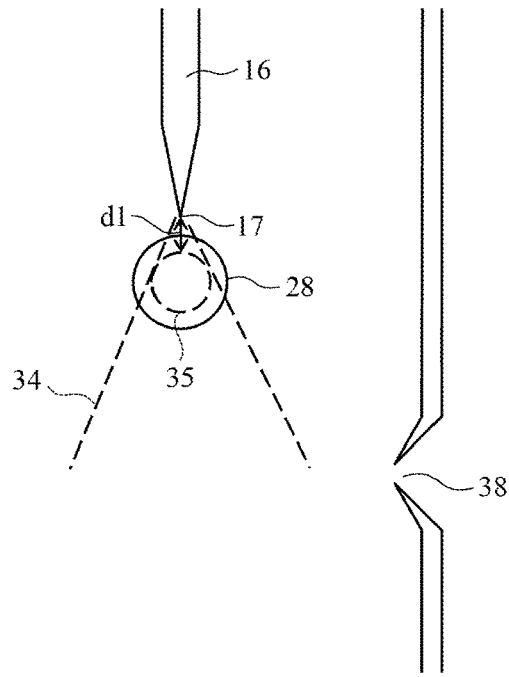
FIG. 5 is a schematic diagram illustrating an example in which the central axis of the spray tip and the central axis of the optical fiber are arranged in a perpendicular positional relationship.

FIG. 4 and FIG. 5 are schematic diagrams illustrating an example in which, as an example of the ESI ion source using the present invention, the central axis of the spray tip and the central axis of the optical fiber are arranged in a perpendicular positional relationship. FIG. 4 is a schematic diagram as viewed from a direction parallel with the optical axis. FIG. 5 is a schematic diagram as viewed from a direction perpendicular to the optical axis.

As illustrated in FIG. 4, in the present example, the central axis of the spray tip 16 and the central axis of the optical fiber 28 are arranged at right angles. By adjusting the laser irradiation position and irradiation width such that the laser light irradiation area 35 is comparable to the sample microparticle spray area 34 in width at the irradiation position, it becomes possible to irradiate the sample microparticles with laser light without waste.

When a jet portion of the sample microparticles with a small spatial expanse is irradiated with laser, because the jet diameter is typically very small such as on the order of 50 the laser beam diameter is also made narrower to a comparable size using a lens, and the portion at a distance of 1 mm from the spray tip distal end 17 is irradiated, for example. The spatial expanse of the sample microparticles is smaller immediately after the spray jet portion than the subsequent plume. Accordingly, laser light absorption efficiency can be increased when the laser light irradiation is focused on the jet of sample microparticles. Thus, a shortest distance d1 between the laser irradiation area 35 and the spray tip distal end is preferably greater than or equal to 0.01 mm and less than or equal to 10 mm, and more preferably in a range of from 0.1 mm to 5 mm. In the present example, d1 is set to 1.0 mm. The spray tip distal end 17 is disposed outside the laser irradiation area 35 so that the tip distal end can be prevented from overheating. As illustrated in FIG. 5, by performing laser light irradiation where the laser light irradiation area 35 and the sample microparticle spray area 34 have comparable diameters, it becomes possible to utilize the energy of laser light for removing solvent from the sample microparticles without waste.

The optical fiber distal end 29 is disposed outside the sample microparticle spray area 34, and a closest distance d2 between the optical fiber distal end 29 and the sample microparticle spray area 34 is 10 mm. As the optical path length becomes shorter, the attenuation rate of laser light becomes smaller and it becomes possible to heat the sample microparticles efficiently. Accordingly, the closest distance d2 is preferably on the order of 0.1 mm to 20 mm, more preferably in a range of greater than or equal to 0.1 mm and less than or equal to 10 mm, and even more preferably in a range of greater than or equal to 0.1 mm and less than or equal to 2 mm.

When the fine spray jet is irradiated with condensed laser light in a focused manner, even a displacement of 0.1 mm in either the axis of laser light, the focal position of laser light, or the axis of the spray tip 16 would result in a large change in the amount of laser hitting the sample. Accordingly, a very precise optical axis adjustment would be required. In addition, if a positional change occurs during a long time of analysis, sensitivity would be greatly varied. Thus, by intentionally increasing the laser diameter to approximately 1 mm, by displacing the focal point for irradiation, or by irradiating the sample plume, it becomes possible to prevent sensitivity variations due to a displacement of the spray tip or the optical fiber. However, in order to secure a laser irradiation efficiency with respect to the sample, it is preferable to irradiate a portion of the plume where the expanse is small, and it is preferable that the laser irradiation area 35 is within 5 mm and not more than 10 mm at a maximum from the spray tip distal end 17. The plume has a width on the order of 20 mm at a distance of 10 mm from the spray tip distal end 17. In view of the requirements that the optical fiber distal end 29 should not contact the sample, and that the distance between the spray tip distal end 17 and the optical fiber distal end 29 should be minimized because a shorter optical path length is associated with a smaller laser light attenuation rate, a distance of approximately 15 mm is necessary between the spray tip distal end 17 and the optical fiber distal end 29 in the orthogonal arrangement.

By adopting the installation relationship such that the axis of the optical fiber 28 is orthogonal to the axis of the minute opening 38, it becomes possible to prevent the entry of laser light into the detector.

Example 2

Figure 6:
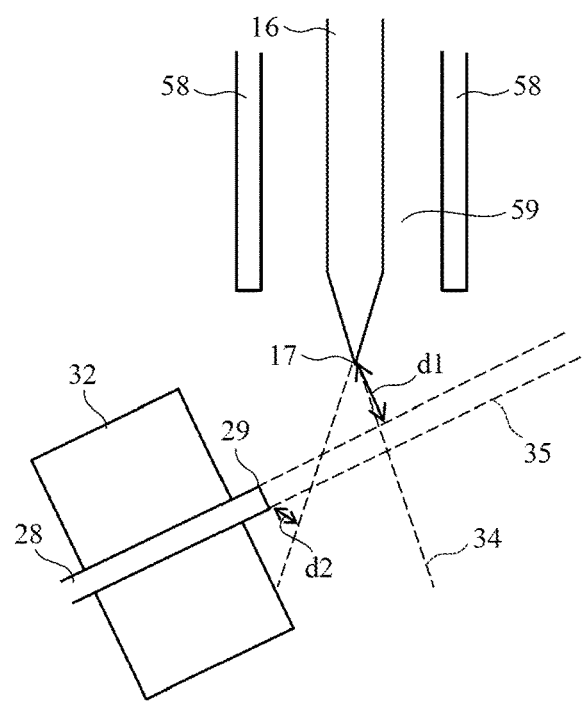
FIG. 6 is a schematic diagram illustrating an example in which the central axis of the spray tip and the central axis of the optical fiber are arranged in an obtuse positional relationship.

FIG. 6 is a schematic diagram illustrating an example in which, as an example of the ESI ion source using the present invention, the central axis of the spray tip and the central axis of the optical fiber are arranged in an obtuse positional relationship.

On the outside of the spray tip 16, a stainless-steel pipe 58 is disposed coaxially with the spray tip 16. Into the stainless-steel pipe 59, an inert gas of nitrogen heated to 200° C. is flowed at a flow rate of 2 L/min in order to promote solvent removal and suppress discharge.

If the distal end 29 of the optical fiber 28 is moved by vibrations and the like, the laser light irradiation position becomes changed, making stable measurement impossible. In order to prevent this, the vicinity of the optical fiber distal end 29 is fixed to the xyz stage of the position adjustor 32. The optical fiber distal end 29 is disposed outside the sample microparticle spray area 34, and the closest distance d2 between the optical fiber distal end 29 and the sample microparticle spray area 34 is 10 mm.

The spray tip distal end 17 is disposed outside the laser irradiation area 35, and the closest distance d1 between the spray tip distal end 17 and the laser irradiation area 35 is 1.0 mm. In this position, a laser beam of the same diameter as the expanse of spray, i.e., 0.5 mm, is irradiated.

In FIG. 6, the spray has an expanse angle of 30 degrees. In order for the optical fiber 28 to not contact the sample microparticles expanding in the sample microparticle spray area 34, it is necessary that the angle between the axis of the spray tip 16 and the axis of the optical fiber 28 is less than or equal to 165 degrees. When the spray expanse angle is greater, it is necessary to reduce the angle between the central axis of the spray tip and the central axis of the optical fiber. Thus, by making the angle between the central axis of the spray tip 16 and the central axis of the optical fiber 28 an obtuse angle, it becomes possible to irradiate the sample microparticles with laser light immediately after a spray without the stainless-steel pipe 58 and the position adjustor 32 interfering with each other.

Example 3

Figure 7:
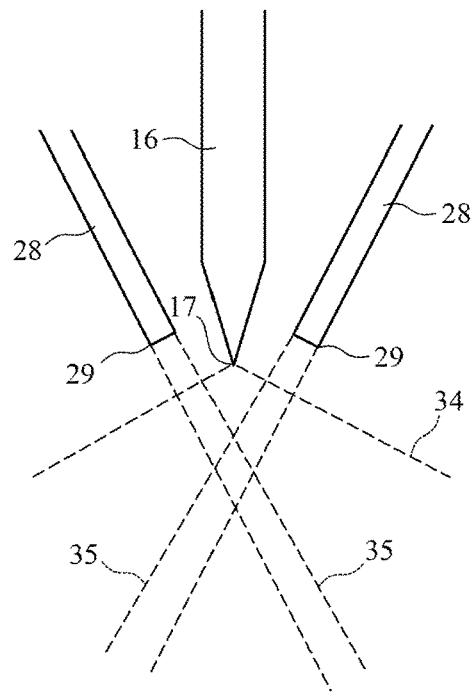
FIG. 7 is a schematic diagram illustrating an example in which the axis of spray tip and the axis of the optical fiber are in an acute positional relationship.
Figure 8:
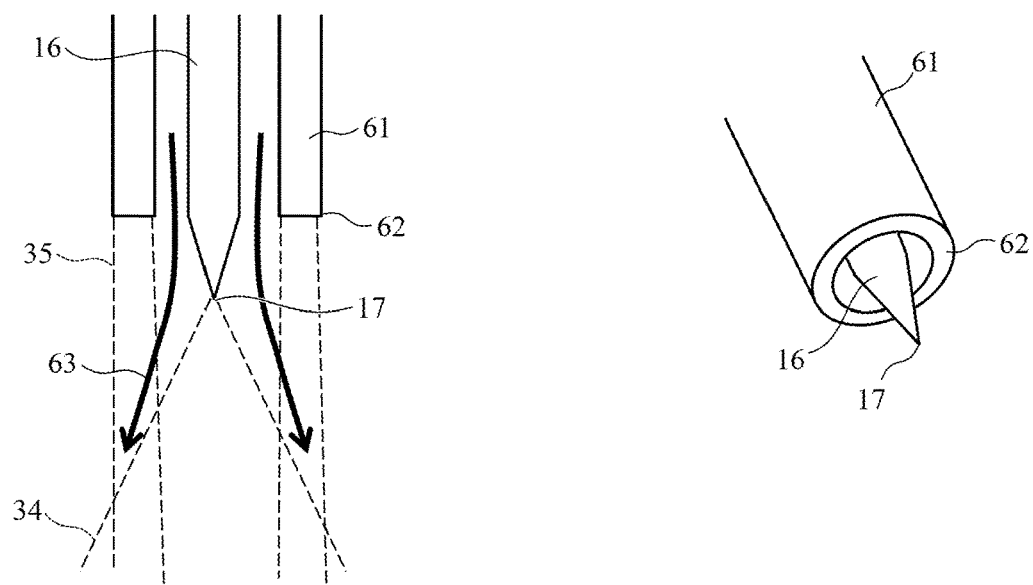
FIG. 8 is a schematic diagram illustrating an example in which the optical fiber is cylindrical.
Figure 9:
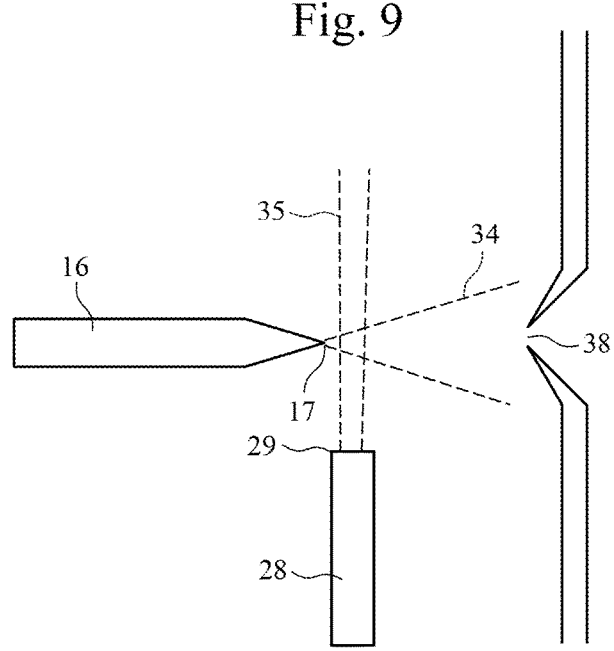
FIG. 9 is a schematic diagram illustrating an example in which the spray tip is in a positional relationship facing a minute opening.
Figure 10:
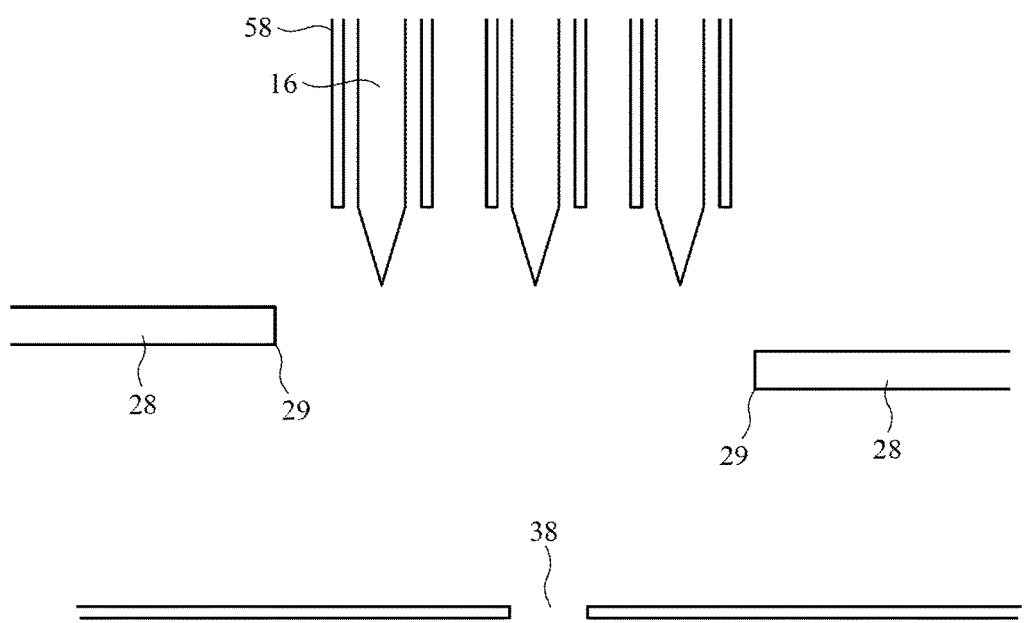
FIG. 10 is a schematic diagram illustrating an example including a plurality of spray tips.
Figure 11:
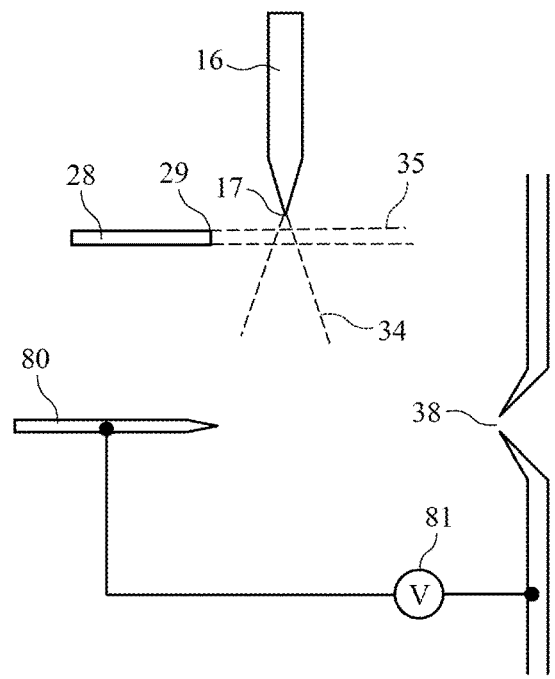
FIG. 11 is a schematic diagram illustrating an example of an APCI ion source in which the present invention is used.

FIG. 7 is a schematic diagram illustrating an example in which, as an example of the ESI ion source using the present invention, the axis of spray tip and the axis of the optical fiber is in an acute positional relationship.

By making the angle between the central axis of the spray tip 16 and the central axis of the optical fibers 28 an acute angle, it becomes possible to perform laser light irradiation without the optical fiber distal end 29 being contaminated by the sample microparticles, even when the sample microparticle spray area 34 is large. The central axis of the spray tip 16 and the central axis of the optical fibers 28 may be parallel with each other. While two optical fibers 28 are arranged in the illustrated example, there may be only one optical fiber 28.

When the angle formed between the central axis of the spray tip 16 and the central axis of the optical fiber 28 is small, only a part of the sample microparticle spray area 34 is irradiated with laser light. Thus, by arranging a plurality of optical fibers at an acute angle with respect to the central axis of the spray tip 16, it becomes possible to increase the irradiation area. In this case, by adopting an arrangement in which the respective optical axes are not on the same plane so that the laser lights from the fibers do not intersect each other, it becomes possible to irradiate the sample microparticles with laser light in a wider spray range.

Example 4

FIG. 8 is a schematic diagram illustrating an example in which, as an example of the ESI ion source using the present invention, the optical fiber is cylindrical.

In the present example, into a hollow tubular optical fiber 61, the spray tip 16 is inserted that has a smaller outer diameter than the inner diameter of the optical fiber 61. From an optical fiber distal end 62, laser light is emitted in a circular-ring shape. By adjusting the distance between the spray tip distal end 17 and the optical fiber distal end 62, it becomes possible to adjust the laser light irradiation area with respect to the sprayed sample. By providing the end face of the optical fiber distal end 62 with an angle, it becomes possible to adjust the direction in which the laser light is emitted.

In addition, by passing nitrogen gas heated to 300° C., for example, through the space between the hollow cylindrical optical fiber 61 and the spray tip 16 as a solvent removal gas 63, it becomes possible to further promote solvent removal and to prevent the sample microparticles from contacting the optical fiber distal end 62. In this configuration, the spray tip, the solvent removal gas introduction pipe, and the optical fiber are integrated, thus requiring a small space for installation. Accordingly, it becomes possible to efficiently perform laser light irradiation from the vicinity of the sample microparticle spray area 34 even when the space for the ion source is narrow and the introduction of the optical fiber is difficult.

Example 5

FIG. 9 is a schematic diagram illustrating an example in which, as an example of the ESI ion source using the present invention, the spray tip is in a positional relationship facing a minute opening.

If the solvent removal efficiency is high and the sample microparticles can be entirely vaporized, there is no concern that the sample microparticles will reach the detector and cause noise. In this case, when a configuration is adopted in which the spray tip 16 directly faces the minute opening 38, the efficiency of introduction of the produced sample ions into the minute opening 38 can be increased and measurement sensitivity is improved. By adopting an arrangement in which the minute opening 38 does not enter the laser irradiation area 35, it becomes possible to prevent the laser light from entering the detector and being detected as noise.

In the case of nano-flow rates, such as the flow rate of a sample solution being 10 to 1000 nL/min, sensitivity is increased by bringing the distance between the spray tip distal end 17 and the minute opening 38 close to approximately 1 mm. Accordingly, by narrowing the laser irradiation area 35 to a beam with a diameter of less than or equal to 0.5 mm, and setting the closest distance between the spray tip distal end 17 and the laser irradiation area 35 to a value in a range of from 0.1 mm to 0.4 mm, the laser light can irradiate only the sample microparticles and not the spray tip distal end 17 and the minute opening 38, and it becomes possible to perform the solvent removal by laser light stably in the case of a nano-flow rate.

Example 6

FIG. 10 is a schematic diagram illustrating an example in which, as an example of the ESI ion source using the present invention, a plurality of spray tips are provided.

It is known that, when a spray is performed at a low flow rate using a spray tip with a small distal end diameter of less than or equal to 1 sample microparticles with a small diameter are generated and solvent removal is facilitated, resulting in an improved ionization efficiency. When the sample solution has a large flow rate, the flow passageway may be diverted, and a plurality of small spray tips 16 may be connected for a spray. Outside each of the spray tips 16, the stainless-steel pipe 58 may be installed, and a solvent removal gas may be flowed therebetween.

When the sample microparticles sprayed from a plurality of spray tips 16 are irradiated with laser light, there may be one optical fiber 28. When the amount of laser irradiation differs between a spray tip close to the optical fiber distal end 29 and a spray tip far therefrom, and a difference is caused in solvent removal efficiency, it becomes possible to perform stable solvent removal by performing irradiation from different directions using a plurality of optical fibers 28.

In this case, if the optical axes of two optical fibers are aligned, laser light may enter opposing optical fibers and damage the laser light source. Accordingly, the optical fibers may be installed with their optical axes displaced from each other.

Example 7

FIG. 11 is a schematic diagram illustrating an example of an atmospheric pressure chemical ionization (APCI) ion source in which the present invention is used.

APCI has the advantage of being able to ionize substances with low polarity that cannot be ionized by ESI, such as alkanes. Without applying a voltage to the spray tip 16, a sample solution is sprayed into the ionization chamber, and non-charged sample microparticles are generated. The microparticles are irradiated with laser light using the optical fiber 28 to promote solvent removal from the sample microparticles, whereby gas phase sample molecules are obtained. Between an APCI needle electrode 80 and the minute opening 38, a voltage is applied from a high-voltage power supply 81, and, by an ion molecule reaction of gas-phase ions formed by corona discharge and the above gas phase sample molecules, the gas phase sample molecules are ionized. The produced gas phase sample molecule ions are fed into the differential evacuation chamber via the minute opening 38. In this configuration, the spray tip functions as a micronization device, and the APCI needle electrode functions as an ionization device.

By this configuration, it becomes possible to perform an analysis of substances that are not ionized by ESI but are ionized by APCI. In the present example, the conditions, such as the positional relationship between the spray tip 16 and the optical fiber 28, are the same as in the other examples.

Example 8

Figure 12:
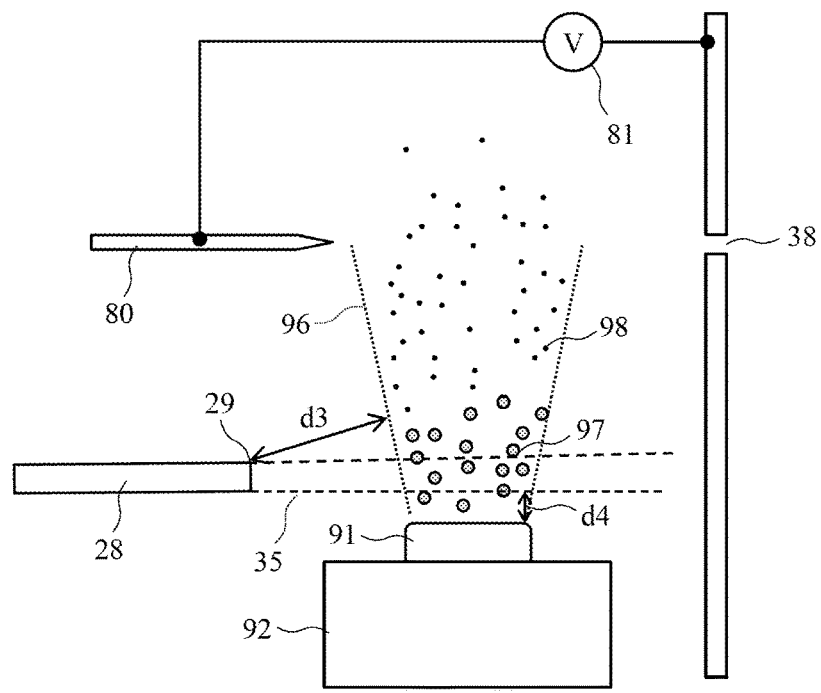
FIG. 12 is a schematic diagram illustrating an example in which an ultrasonic atomizer is used as a sample micronization device.

FIG. 12 is a schematic diagram illustrating an example in which, as an example of the APCI ion source using the present invention, an ultrasonic atomizer is used as a sample micronization device.

A liquid sample 91 is placed on an ultrasound vibrator 92, and sample microparticles 97 are generated by ultrasound atomization. In this case, the ultrasound vibrator provides the function of a sample holding unit and a micronization device. Other atomization methods may be employed, such as blowing a gas. The sample microparticles 97 are irradiated with laser light via the optical fiber 28 for solvent removal, and neutral gas phase sample molecules 98 that have no charge are formed. By applying a high-voltage between the APCI needle electrode 80 and the minute opening 38 from the high-voltage power supply 81, a corona discharge is caused, forming gas-phase ions. The gas-phase ions cause an ion molecule reaction with the gas phase sample molecules 98, whereby the gas phase sample molecules 98 are ionized. A closest distance d3 between the optical fiber distal end 29 and a sample microparticle spray area 96 is preferably in a range of 0.1 mm and 20 mm. In the present example, the closest distance d3 is on the order of 10 mm. A closest distance d4 between the surface of the sample 91 and the laser irradiation area 35 is preferably greater than or equal to 0.01 mm and less than or equal to 10 mm, and more preferably greater than or equal to 0.1 mm and less than or equal to 5 mm. In the present example, d4 is on the order of 1 mm, and the laser light does not irradiate either the liquid sample 91 or the ultrasound vibrator 92. By this positional relationship, it becomes possible to perform highly efficient solvent removal without the optical fiber distal end 29 being contaminated by the sample, and without the sample 91 being caused to bump and becoming scattered. In this case, the closest distance between the optical fiber distal end 29 and the ultrasound vibrator 92 is preferably greater than or equal to 1 mm and less than or equal to 20 mm. In the present example, the closest distance is approximately 5 mm.

The configuration of the example makes it possible to obtain high ionization efficiency through the efficient solvent removal using an optical fiber even with respect to a spot of liquid sample dropped onto a plate. The configuration may also be applied to solid samples, such as powder.

As the ionization method, means other than APCI may be used. Examples include atmospheric pressure photoionization (APPI) whereby ionization is performed by exciting a sample molecule or matrix using optical energy; and dielectric barrier discharge ionization whereby ionization is performed by causing gas-phase ions generated by a dielectric barrier discharge using an alternating current electric field to react with a gas phase sample molecule. By selecting the ionization method in accordance with the chemical properties of the sample of interest, it becomes possible to improve the sensitivity of analysis.

Example 9

Figure 13:
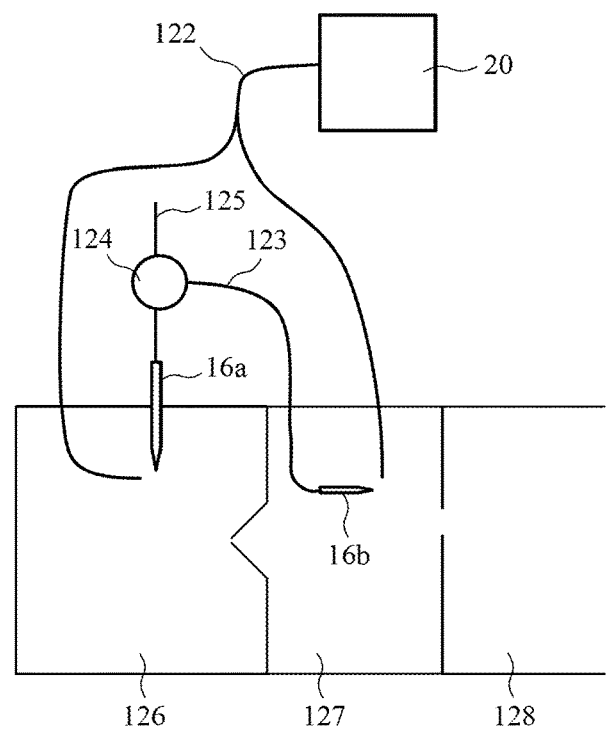
FIG. 13 is a schematic diagram illustrating an example of an ESI ion source in which the present invention is used.

FIG. 13 is a schematic diagram illustrating an example of an ESI ion source in which the present invention is used.

A sample with a flow rate of the order of from 10 μL/min to 1 mL/min delivered from an LC or a syringe pump or the like is sprayed from a spray tip 16a into an atmospheric pressure section 126, and the sample is ionized. A flow passageway 125 is fitted with a flow splitter 124 that diverts the sample at a constant rate. The sample diverted from the flow passageway 125 into the flow passageway 123 via the flow splitter 124 at a low flow rate on the order of 100 nL/min is sprayed from the spray tip 16b into a low vacuum section 127, and ionized by ESI. The ionized sample is moved to a vacuum section 128 having a lower pressure than the low vacuum section 127, and subjected to mass spectrometry. The spray tip 16b has a distal end inner diameter on the order of 1 μm to 10 μm designed for small nano-flow rates.

Infrared light produced in the laser light source 20 passes through an optical fiber 122 and is diverted midway and introduced into the atmospheric pressure section 126 and the low vacuum section 127, where the infrared light irradiates the spray to improve solvent removal efficiency. While FIG. 13 illustrates two ion sources connected in series with respect to the mass spectrometry unit, the two ion sources may be connected in parallel. The configuration makes it possible to improve the solvent removal efficiency of a plurality of ion sources with a single laser light source.

If sensitivities are comparable between when atmospheric pressure ionization is performed using a high flow rate and when low vacuum ionization is performed using a low flow rate, it becomes possible to double the sensitivity by performing ionizations with both ion sources simultaneously. Conversely, if one of the case of atmospheric pressure ionization with a high flow rate and the case of low vacuum ionization with a low flow rate has a sensitivity 10 times greater than or equal to that of the other, it becomes possible to substitute the splitter 124 with a selection valve, and to selectively use the ion source with a higher sensitivity.

Example 10

Figure 14:
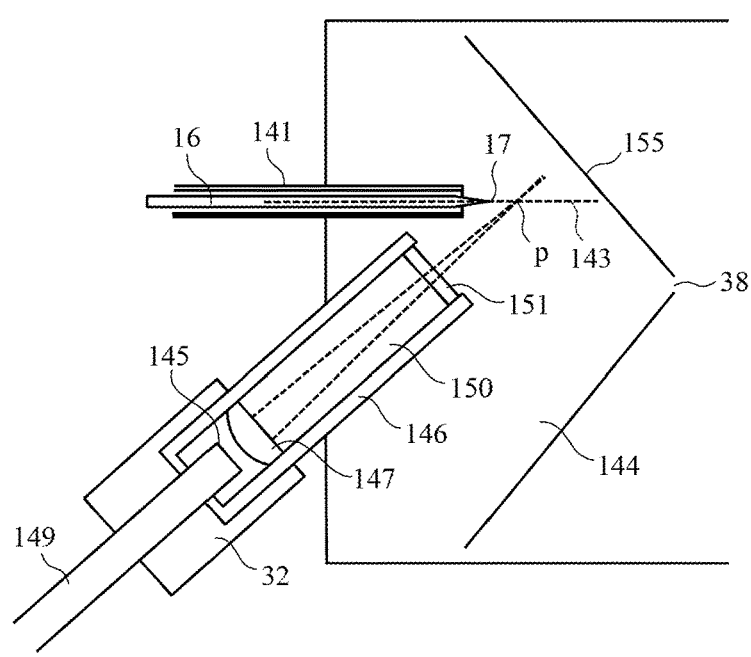
FIG. 14 is a schematic diagram illustrating an example of an ESI ion source in which the present invention is used.
Figure 15:
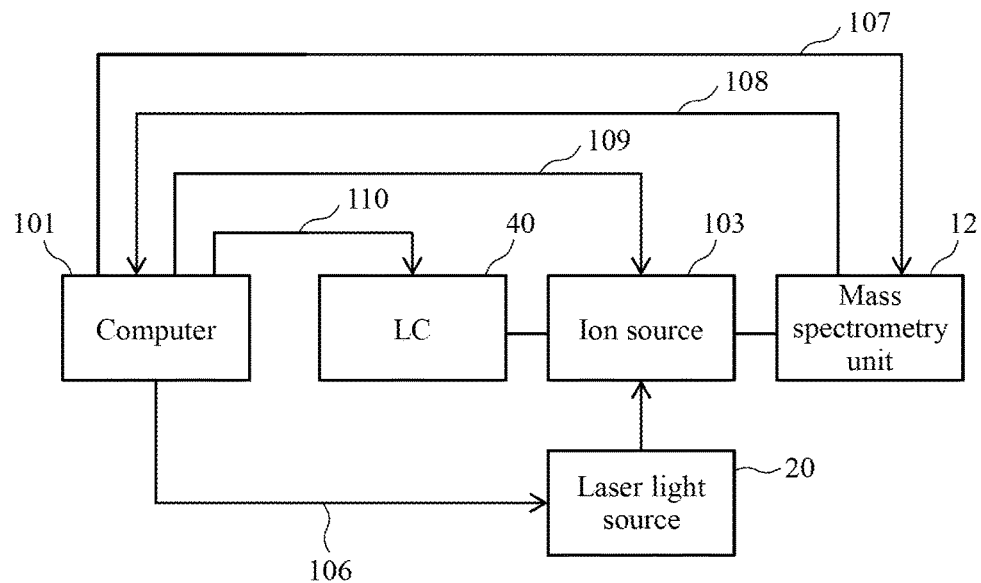
FIG. 15 is a diagram illustrating an example of a mass spectrometry system in which the present invention is used.
Figure 16:
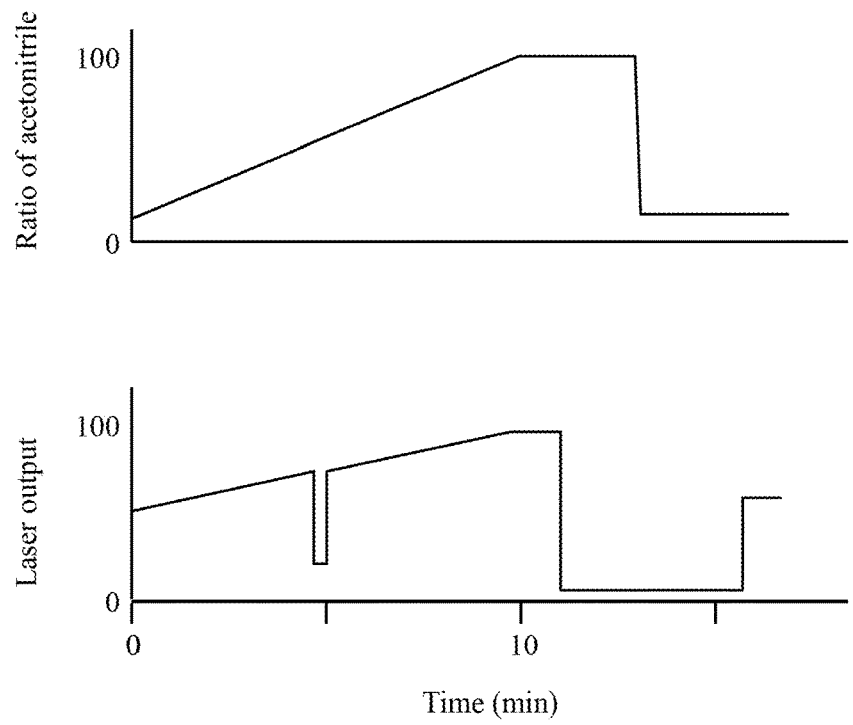
FIG. 16 illustrates an example of a control sequence in the mass spectrometry system according to an example.

FIG. 14 is a schematic diagram illustrating an example of the ESI ion source using the present invention.

From the ESI spray tip 16, a sample solution is sprayed at 10 μL/min. Between the sample solution and a mortar-shaped counter electrode 155, a voltage of 3 kV is applied. The outside of the spray tip 16 is surrounded by a double pipe 141. Between the outer pipe and the inner pipe, 200° C. of carbon dioxide gas is flowed as heating gas at a flow rate of 1 L/min to promote solvent removal and suppress spray expansion. Infrared laser generated from an infrared laser light source (thulium fiber laser, wavelength 1.94 µm, output 0.5 W) is emitted from an optical fiber 149 in the form of parallel light with a diameter of 6 mm, enters a quartz plano-convex lens 147 with a diameter of 12 mm, and is condensed at a focal distance of 100 mm. The diameter of the expanse of light at the focal point is 64 µm. The optical axis of infrared laser and the axis 143 of the spray tip 16 intersect with each other at a point p. The position of the optical fiber 149 is adjusted using the xyz stage of the position adjustor 32 so that the focal point of infrared laser is in the vicinity of p. In this case, a visible light laser may be caused to enter via the same optical path as the infrared laser, whereby position adjustment can be facilitated.

Use of a lens with a longer focal distance enables a decrease in the degree of expansion of light at a location deviated from the focal position, and facilitates position adjustment. However, irradiation of a spray at a long distance results in the absorption of infrared light by water vapors and the like in the space, and a means for preventing this is necessary. Accordingly, in the present example, the distal end of the optical fiber 149 and the lens 147 are fixed in a stainless-steel pipe 146, and the stainless-steel pipe 146 is sealed with an infrared transmission window 151 made of quartz provided in the pipe exit. A pipe inner portion 150 has dried air enclosed therein, thus providing a light guide path that does not interfere with the transmission of infrared laser due to the entry of external water vapor into the pipe inner portion 150.

The stainless-steel pipe 146 has an outer diameter of 20 mm. The central axis of the spray tip 16 and the central axis of the stainless-steel pipe 146 form an angle of 45 degrees. The distance from the surface of the infrared transmission window 151 to the point p is approximately 15 mm. The distance between the spray tip distal end 17 and the point p is 1 mm. Besides such straight pipe, the stainless-steel pipe 146 may have a tapering shape with a distal end outer diameter of less than or equal to 10 mm. By decreasing the distal end outer diameter of the pipe, the distance from the surface of the infrared transmission window 151 to the focal point p can be made close to less than or equal to 10 mm, and it becomes possible to decrease the rate of absorption of infrared laser by the solvent vapor.

In addition, in the present example, while an ionization chamber 144 has the atmospheric pressure, by depressurizing to approximately 0.01 atm, it becomes possible to similarly decrease the rate of absorption of infrared laser by the solvent vapor. Pressures of less than or equal to 0.01 atm are not desirable because discharge may easily occur and ionization may become unstable.

While the location of irradiation of the spray with infrared laser is estimated to be a boundary area between the spray jet and plume, many of conventional ion sources are not equipped with a mechanism for measuring the spray expanse. Thus, by moving the infrared laser in the optical axis direction so as to distance the focal point away from the point p, and monitoring the sample peak intensity of mass spectrometry while increasing the laser irradiation diameter with respect to the spray to search for a laser position with the highest sensitivity, it becomes possible to find an optimum laser irradiation diameter with respect to the spray expanse. With regard to the distance between the infrared transmission window 151 and the spray tip distal end 17, at least 1 mm is necessary as a likelihood required for position adjustment. It is also preferable that a portion at a distance of 0.1 mm to 10 mm from the spray tip distal end 17 is irradiated with laser with a diameter on the order of 0.1 mm, and that the distance from the infrared transmission window 151 to the point p is less than or equal to 20 mm. While in the present example, the central axis of the spray tip 143 and the laser light axis form an angle of 45 degrees, interference of the spray tip 16, the stainless-steel pipe 146, and the counter electrode 155 can be avoided as long as the angle is on the order of 10 degrees to 80 degrees. From the foregoing, the closest distance between the spray tip distal end 17 and the infrared transmission window 151 is in a range of from 1 mm to 20 mm. When the distance is decreased to 1 mm, discharge may occur between the spray tip distal end 17 and the stainless-steel pipe 146. Accordingly, the pipe material preferably comprises an insulator.

With the above configuration, it becomes possible to easily optimize the laser irradiation position while also preventing attenuation due to the absorption of infrared laser by the solvent vapor.

Example 11

FIG. 15 is a diagram illustrating an example of a mass spectrometry system in which the present invention is used.

The mass spectrometry system of the present example includes a computer 101, the LC 40, an ion source 103, the mass spectrometry unit 12, and the laser light source 20.

The computer 101 sends LC parameters 110, such as flow rate, solvent composition, and amount of sample to the LC 40; mass spectrometry parameters 107, such as mass range, separation time, and voltage, to the mass spectrometry unit 12; ion source parameters 109, such as voltage, temperature, and gas flow rate, to the ion source 103; and laser parameters 106, such as wavelength and output, to the laser light source 20. The computer 101 also sets an appropriate laser light wavelength or output in accordance with the type of sample or the LC method. For example, the computer 101 makes settings such as: selecting the wavelength in accordance with the solvent type or composition; turning off the laser light during the time in which a sample that easily thermally degrades is eluted; and increasing the output when the sample solution has a large flow rate. Mass spectrometry data 108 detected in the mass spectrometry unit 12 are sent to the computer 101 for analysis.

FIG. 16 illustrates an example of a control sequence according to the mass spectrometry system of the present example.

The LC solvent has a linear gradient in a period of 10 minutes from water:acetonitrile=90:10 to 0:100, and in the ESI ion source, a continuous-oscillation infrared laser with a wavelength of 1.9 μm having an absorption peak for water is irradiated. The extinction coefficient of water at the wavelength of 1.9 μm is approximately 100 $cm^{-1}$, and in a solvent of 100% water, light is transmitted or absorbed to the depth from the liquid surface on the order of 1/100 cm=0.1 mm. Accordingly, with respect to droplets with a diameter on the order of 0.1 mm, the entire droplets can be uniformly heated. The output of the laser light source 20 can be externally controlled by the computer 101, and the output is increased as the proportion of water decreases during gradient elution. The output is decreased during the time in which substance that is dissociated by infrared light irradiation is eluted, such as a complex molecule formed of a hydrogen bond, or the time in which no analysis is performed, such as the equilibrating time.

In the example illustrated in FIG. 16, a photodegradable substance is eluted at the time of five minutes. Accordingly, the laser output is decreased to 20% at 4.9 to 5.1 minutes, in light of the variation of ±0.1 minute for a hold time. In addition, because the sample elution ends at the time of 11 minutes, the laser output is decreased to 5% following the 11 minutes, and returned back to the initial output value at the 16 minutes in preparation for the next analysis.

With this configuration, it becomes possible to program and execute an optimum laser irradiation adapted for the purpose of analysis.

The present invention is not limited to the foregoing examples, and may include various modifications. The examples have been described in detail for facilitating an understanding of the present invention, and are not necessarily limited to those provided with all of the configurations that have been described. A part of the configuration of one example may be replaced with the configuration of another example, or the configuration of the other example may be incorporated into the configuration of the one example. With respect to a part of the configuration of each example, addition, deletion, or substitution of other configurations may be made.

REFERENCE SIGNS LIST

10 Ionization chamber
11 Differential evacuation unit
12 Mass spectrometry unit
16 Spray tip
22 Mass separation device
23 Detector
28 Optical fiber
30 Gas introduction pipe
31 Lens
32 Position adjustor
33 Sample microparticles
34 Sample microparticle spray area
35 Laser irradiation area
38 Minute opening
58 Stainless-steel pipe
61 Tubular optical fiber
80 Needle electrode
91 Liquid sample
92 Ultrasound vibrator
96 Sample microparticle spray area
144 Ionization chamber
146 Stainless-steel pipe
149 Optical fiber
151 Infrared transmission window
155 Counter electrode

The invention claimed is:

1. An ionization device for ionization of a substance, the ionization device comprising:

a sample holding unit that holds a sample including a target substance;

a micronization device that turns the sample being held by the sample holding unit into sample microparticles;

a light source; and a light guide path that guides light from the light source to the sample microparticles generated by the micronization device to irradiate the sample microparticles, wherein a closest distance between a spatial area in which the sample microparticles are present and a distal end of the light guide path is greater than or equal to 0.1 mm and less than or equal to 20 mm, and a closest distance between an area of light irradiation by the light guide path and any of a surface of the sample, the micronization device, and the sample holding unit that is the closest is greater than or equal to 0.01 mm and less than or equal to 10 mm.

2. The ionization device according to claim 1, wherein the closest distance between the spatial area in which the sample microparticles are present and the distal end of the light guide path is greater than or equal to 0.1 mm and less than or equal to 10 mm.

3. The ionization device according to claim 1, wherein the closest distance between the spatial area in which the sample microparticles are present and the distal end of the light guide path is greater than or equal to 0.1 mm and less than or equal to 2 mm.

4. The ionization device according to claim 1, wherein the closest distance between the area of light irradiation and any of the surface of the sample, the micronization device, and the sample holding unit that is the closest is greater than or equal to 0.1 mm and less than or equal to 5 mm.

5. The ionization device according to claim 1, wherein the micronization device performs the micronization by spraying a liquid sample.

6. The ionization device according to claim 1, wherein the micronization device is an electrospray.

7. The ionization device according to claim 1, wherein a gas-phase ion formed by a corona discharge is ionized through a reaction with a gas phase sample molecule generated from the sample microparticles.

8. The ionization device according to claim 1, wherein a gas-phase ion formed by a dielectric barrier discharge is ionized through a reaction with a gas phase sample molecule generated from the sample microparticles.

9. The ionization device according to claim 1, comprising a gas introduction unit for introducing a solvent removal gas around the sample microparticles.

10. The ionization device according to claim 1, wherein an ionized sample is sent to a mass separation device, an ion mobility meter, or a high-field asymmetric ion mobility spectrometer for detection.

11. The ionization device according to claim 1, comprising a position adjustor that fixes a distal end portion of the light guide path, and that adjusts a positional relationship between the light guide path and the sample, the sample holding unit, or the micronization device.

12. The ionization device according to claim 1, wherein the light guide path is an optical fiber.

13. The ionization device according to claim 12, comprising a plurality of optical fibers.

14. The ionization device according to claim 12, wherein the optical fiber is hollow.

15. The ionization device according to claim 14, wherein the hollow optical fiber has a solvent removal gas passed therethrough.

16. The ionization device according to claim 1, wherein the light source is an infrared laser light source.

17. The ionization device according to claim 16, wherein the infrared laser has a wavelength of greater than or equal to 1 μm and less than or equal to 100 μm.

18. The ionization device according to claim 1, wherein the micronization device is in a pressure range of greater than or equal to 0.01 atm and less than or equal to 1 atm.

19. The ionization device according to claim 1, comprising a plurality of micronization devices that spray the liquid sample.

20. The ionization device according to claim 10, wherein an ion detector of the mass separation device, the ion mobility meter, or the high-field asymmetric ion mobility spectrometer is deviated from the area of light irradiation.

21. The ionization device according to claim 1, comprising a plurality of ionization chambers, wherein, from the single light source, light is introduced into the plurality of ionization chambers via a plurality of light guide paths.

* * * * *